US009826766B2

(12) United States Patent
Guerin-Deremaux et al.

(10) Patent No.: US 9,826,766 B2
(45) Date of Patent: Nov. 28, 2017

(54) USE OF POLYSACCHARIDES FOR THE INTESTINAL WELL-BEING OF NURSING INFANTS AND/OR INFANTS

(71) Applicant: ROQUETTE FRERES, Lestrem (FR)

(72) Inventors: Laetitia Guerin-Deremaux, Nieppe (FR); Virginie Teichman-Dubois, Laventie (FR); Daniel Wils, Morbecque (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 14/442,802

(22) PCT Filed: Nov. 13, 2013

(86) PCT No.: PCT/FR2013/052724
§ 371 (c)(1),
(2) Date: May 14, 2015

(87) PCT Pub. No.: WO2014/076415
PCT Pub. Date: May 22, 2014

(65) Prior Publication Data
US 2015/0296850 A1 Oct. 22, 2015

(30) Foreign Application Priority Data

Nov. 14, 2012 (FR) .................. 12 60837

(51) Int. Cl.
A61K 31/718 (2006.01)
A23L 1/29 (2006.01)
A23L 29/30 (2016.01)
A23L 33/00 (2016.01)
A23L 33/115 (2016.01)
A23L 33/135 (2016.01)
A23L 33/15 (2016.01)
A23L 33/21 (2016.01)

(52) U.S. Cl.
CPC .............. *A23L 1/296* (2013.01); *A23L 29/35* (2016.08); *A23L 33/115* (2016.08); *A23L 33/135* (2016.08); *A23L 33/15* (2016.08); *A23L 33/21* (2016.08); *A23L 33/40* (2016.08); *A61K 31/718* (2013.01); *A23C 2240/15* (2013.01); *A23V 2002/00* (2013.01)

(58) Field of Classification Search
None
See application file for complete search history.

(56) References Cited

U.S. PATENT DOCUMENTS

| 6,630,586 | B1 | 10/2003 | Fouache et al. |
| 7,932,238 | B2* | 4/2011 | Wils .................. A61K 31/718 514/54 |
| 8,871,740 | B2* | 10/2014 | Guerin-Deremaux . A61K 31/55 514/54 |
| 2008/0182821 | A1 | 7/2008 | Wils et al. |
| 2011/0017059 | A1* | 1/2011 | Heren .................. F03C 1/0403 91/491 |
| 2011/0110907 | A1* | 5/2011 | Deremaux ........... A61K 31/715 424/93.51 |
| 2011/0117059 | A1 | 5/2011 | Deremaux et al. |
| 2012/0172319 | A1 | 7/2012 | Chow et al. |

FOREIGN PATENT DOCUMENTS

| EP | 1 006 128 A1 | 6/2000 |
| FR | 1 251 810 A | 3/1960 |
| FR | 2 935 228 A1 | 3/2010 |
| FR | 2 974 512 A1 | 11/2012 |
| WO | 2012/089784 A1 | 7/2012 |
| WO | WO2012/089784 | * 7/2012 ............. A61K 35/74 |

OTHER PUBLICATIONS

Mansson, Helena Lindmark, "Fatty Acids in Bovine Milk Fat" Food and Nutrition Research (2008), pp. 1-3.*
Commission Directive 2006/141/EC of Dec. 22, 2006 on infant formulae and follow-on formulae and amending Directive 1999/21/EC (Text with EEA relevance), Official Journal of the European Union, (Acts whose publication is obligatory), The Commission of the European Communities, 2006, 12, 30.
International Search Report, dated Feb. 7, 2014, from corresponding PCT application.

* cited by examiner

*Primary Examiner* — Eric S Olson
(74) *Attorney, Agent, or Firm* — Blank Rome LLP

(57) ABSTRACT

The use of a polysaccharide in a method for improving the flora of the colon of nursing infants and/or infants, thus treating or preventing colic and enterocolitis and therefore improving and/or generally stimulating the intestinal well-being of nursing infants and/or infants. A food composition for feeding nursing infants and/or infants, including at least one polysaccharide for treating or preventing colic and enterocolitis and improving and/or stimulating the intestinal well-being of nursing infants and/or infants. The polysaccharide used is a branched maltodextrin, preferably with a molecular mass of between 400 and 4500.

12 Claims, No Drawings

USE OF POLYSACCHARIDES FOR THE INTESTINAL WELL-BEING OF NURSING INFANTS AND/OR INFANTS

FIELD OF THE INVENTION

The present invention relates to the use of a polysaccharide for improving the flora of the colon of infants and/or young children, and thus treating or preventing colic and enterocolitis and therefore improving and/or generally promoting the intestinal well-being of infants and/or young children.

The present invention also relates to a food composition for feeding infants and/or young children, comprising at least one polysaccharide for treating or preventing colic and enterocolitis and improving and/or promoting the intestinal well-being in infants and/or young children.

TECHNICAL BACKGROUND

The intestinal flora represents in the host organism a real ecosystem, establishing close connections with the digestive epithelia and the immune system which is associated therewith. The interactions between the various bacteria, just as between the bacteria and their host, are factors in the control of the equilibrium of the microbial flora and the development of certain acute or chronic pathological conditions. The digestive flora also participates in a certain number of functional activities and interferes with the digestion and absorption of certain nutrients. The significant role of the intestinal flora in human health was recognized at the beginning of the $20^{th}$ century by the consideration that a certain number of diseases could be the consequence of a breaking of the equilibrium of the intestinal flora, and that the restoring of this equilibrium was beneficial in terms of health. However, the idea of incorporating microorganisms into the human diet or at least using the potential beneficial effects of the presence of these microorganisms appears to go back to very ancient times.

The intestinal ecosystem is established during the first months of life. Indeed, infants have no intestinal flora at birth. In utero, the intestine is sterile.

In newborn babies, the colonization of the digestive tract is relatively stereotyped during the first days, depending partly on the composition of the maternal vaginal and fecal flora; it is delayed in children born by cesarian. Bifidobacteria and *Lactobacilli*, and to a lesser extent *Bacteroides* and Clostridiae, appear as early as the third day. The implantation of this flora is directly dependent on the type of diet received, on the environmental conditions and on any prescription of antibiotics.

At the end of the first month, very clear differences exist in the composition of the intestinal flora according to the type of diet received by the newborn baby. Thus, the intestinal flora of breast-fed children is almost exclusively composed of Bifidobacteria. There are numerous bifidogenic factors in maternal milk and they could not be limited to only galactooligosaccharides.

On the other hand, the flora of babies fed with infant milks is rich in Enterobacteria and Gram-negative bacteria. As soon as the diet begins to be diversified, the difference between the flora of breast-fed children and that of artificially fed children becomes less marked, with an increase in the concentration of *Escherichia coli*, Enterococcaceae and Clostridiaceae. Between the age of one year and two years, the child acquires an intestinal flora that is virtually identical to that of the adult. This microflora remains relatively stable during the lifetime, except in the case of drastic changes in diet, of treatment with antibiotics, or of modulation through the ingestion of prebiotics or probiotics.

The term infant colic (IC) usually refers to a clinical entity characterized by the paroxysmal occurrence in an infant of less than three months of prolonged crying and of phases of agitation, the cause of which is presumed to be of intestinal origin. IC is often due to the fact that the infant, thus far fed directly via the umbilical cord and its bloodstream, has made very little usage of its digestive tract and even less of its stomach. In the first months, the adaptation of the digestive system, induced by digestion, produces digestive pain in the baby, called colic. The ingestion of air during feeding worsens the phenomenon since this produces gases. The term colic is used only if the infant is otherwise in good health and its weight is normal. It generally occurs at the end of the afternoon, after a meal. The child is agitated, folds its legs against its stomach, cries and is inconsolable until it finally emits a gas. IC does not necessarily have an effect on the stools of the infant, which generally remain normal.

The term enterocolitis, and more specifically the term necrotizing enterocolitis (NEC), denotes a pathological condition that is more serious, or even lethal in more severe cases. It is the result of various attacks which are often intricate. NEC is an inflammation of the small intestine or of the colon leading to frequent and not very consistent stools, which may be painful. It is an acquired pathological condition of newborn babies which is defined by the occurrence of multifocal necrosis of the intestinal wall characterized by the appearance of ischemic and hemorrhagic necrotic patches which can lead to ulcerations capable of progressing to digestive perforation. NEC usually occurs in premature newborn babies, between the $3^{rd}$ and the $10^{th}$ day of life; it is exceptional in full-term newborn babies. It results from a multifactorial attack of the mucosa. The physiopathology of NEC is multifactorial. Prematurity is the principal factor thereof. Finally, the digestive stasis, the enteral feeding and the immunological immaturity of newborn babies is thought to promote the occurrence of NEC. Dangerous and pathogenic microorganisms have been isolated in blood cultures and peritoneal fluid from newborn babies suffering from NEC: *Escherichia coli, Klebsiella pneumoniae, Pseudomonas aeruginosa, Staphylococcus aureus, Enterococcus faecalis* and also anaerobic bacteria responsible for severe forms with pneumatosis. There is constant degradation of the general condition, but the clinical picture is variable, ranging from the existence of isolated digestive signs (bloated and painful abdomen, bilious vomiting, arrest of transit) to that of septic signs (grayish complexion, hypothermia, apnea, state of oligoaneuric shock) in the severe forms.

Thus, in the first months of life, the colonization of the digestive tract is an essential step. Moreover, throughout life, a certain bacterial equilibrium must be ensured in order to maintain constant digestive well-being in the child and then in the adult.

The digestive tract is colonized by a very important microflora, implanted essentially in the colon, with great diversity since it is composed of more than 400 different species.

The role of a balanced intestinal flora is very important. The flora is involved in the degradation of polysaccharides, the fermentation of monosaccharides, the conversion of xenobiotics, the proteolysis of amino acids, the production of fermentative hydrogen and reuse thereof, the production of intestinal gases, the metabolism of bile acids, and the production of mutagens, but also and especially at the level of the development of the intestinal immune system (gut associated lymphoid tissue).

Thus, the equilibrium of the intestinal flora participates in regulating intestinal transit, in preventing the penetration of hostile antigens and in preventing the proliferation of pathogenic microorganisms. Many and often concomitant mechanisms are cited to account for the inhibition of pathogenic flora:

production of inhibiting substances such as organic acids, in particular of lactic acid, of hydrogen peroxide ($H_2O_2$), occupation of adhesion sites on the intestinal mucosa or on the mucus coating it, thus thwarting the possibility for other microorganisms to attach thereto, degradation of toxin receptor sites, stimulation of immune functions, such as the production of immunoglobulins A (IgAs). IgAs are an antibody isotype predominantly produced at the level of the mucosae, where they constitute a first line of immune defense against toxins and infectious agents present in the environment. In the intestine, IgA production is strongly induced during the colonization of newborn babies by the intestinal flora, acquired during delivery and in the hours which follow, competition with respect to nutrients.

A growing interest has seen the light of day for the ecological control of the intestinal flora in human beings, and more particularly that of infants and of young children, through the administration of ingredients which can be categorized as three types:

Prebiotics are defined as a non-digestible substance which induces a physiological effect beneficial to the host by specifically stimulating the growth and/or the activity of a limited number of bacterial populations already established in the colon. This definition does not emphasize one bacterial population in particular. It is commonly accepted that a prebiotic increases the number of bifidobacteria and of lactic acid-producing bacteria, since these groups of bacteria are beneficial to the host. Thus, prebiotics are present in the intestinal lumen and stimulate the selective growth of a flora considered to be beneficial in terms of health. The key to their effectiveness is that they can be fermented by a specific intestinal microflora of which the development thus generated will be beneficial. This mode of action thus involves regular ingestion of the ingredient concerned. As a result, a certain number of studies have attempted to identify the potentially bifidogenic factors and certain oligosaccharides have ranked among the best of the candidates. Non-digestible oligosaccharides withstand hydrolysis by brush border enzymes and will behave like energy substrates for certain elements of the colonic flora, such as *lactobacilli* and bifidobacteria. The bifidogenic effect of prebiotics, and also their potential immunometabolic action, suggests that they may have a beneficial effect in particular in the context of the prevention of intestinal infections.

Probiotics are microorganisms which, once ingested, are capable of remaining alive during intestinal transit and of modifying the intestinal flora while having a demonstrated beneficial effect on the health; this is the major factor which determines the effectiveness thereof. The probiotics used are lactic acid-producing live micro-organic strains, such as *lactobacilli*, certain streptococci and bifidobacteria. Certain strains are, furthermore, capable of having an immunoregulatory role, in particular by stimulating IgA production and phagocytic capacity.

Symbiotics are defined as a product containing both one or more probiotic(s) and one or more prebiotic(s). The presence of prebiotic(s) exerts a beneficial effect on the stability of the probiotic(s) in the product and also on survival thereof and implantation thereof in the gastrointestinal tract, as long as the prebiotic is present.

Among the numerous prebiotic candidates, the most well known and studied are fructans (FOSs: fructooligosaccharides, oligofructose and inulin) and other oligosides of galactose and transgalactose (GOSs and TOSs). The lactose, which escapes digestion in the small intestine, is also a prebiotic, and several studies have shown that lactose can reach the colon in infants. Numerous other carbohydrates could claim the name prebiotics (xylooligosaccharides, isomaltooligosaccharides, glucooligosaccharides, etc.). Some resistant starches and alcohol sugars could also have prebiotic properties. Lactulose is also a prebiotic.

The prebiotic ingredient must be perfectly characterized. The products or organisms responsible for the ingredient must be known and characterized, whether it is a question of an ingredient isolated from a vegetable, animal or microbial product, or of an ingredient produced by chemical or microbial synthesis.

The market for food products intended for infants and children under the age of three, who are in good health, has, for more than a century, always been, constantly driven by the companies which design and/or market these foods, in constant evolution. Today, European regulations, transcribed into national law, define in a more sophisticated manner the composition of the two types of milk formulae authorized for marketing, that is to say infant formulae (for children born at full term, from birth to 4 to 6 months), and follow-on formulae (for infants aged from 4-6 months to 12 months). The evolution of the compositions of these milk formulae has thus constituted considerable progress in terms of infant nutrition. The better adaptation to the nutritional needs and digestive capacities of young children of the protein, lipid and carbohydrate formula and of the mineral salt, trace element and vitamin contents has meant that, when the mother cannot or does not want to breastfeed, or when breastfeeding after the age of six months is no longer sufficient, these formulae make it possible to obtain normal somatic growth, and satisfactory psychomotor development, without any major pathological risk.

Armed with this finding and after numerous research studies, it is to the applicant companies' credit to have overcome all the demands required in infant nutrition by proposing a novel composition for feeding infants and/or young children. More specifically, the present invention relates to the field of prebiotics in infant nutrition.

SUMMARY OF THE INVENTION

The present invention relates to the use of a polysaccharide for improving the flora of the colon of newborn babies and/or young children, and thus treating or preventing colic and enterocolitis and improving and/or generally promoting the intestinal well-being of infants and/or young children.

The present invention also relates to the treatment and/or the prevention of colic and enterocolitis and the improvement and/or promotion of the intestinal well-being in infants and/or young children.

The present invention also relates to a food composition for feeding infants and/or young children, comprising at least one polysaccharide for treating or preventing colic and enterocolitis and improving and/or promoting the intestinal well-being in infants and/or young children.

DETAILED DESCRIPTION OF THE EMBODIMENTS

The present invention relates to the use of branched maltodextrins for improving the flora of the colon of newborn babies and/or young children, and thus treating or preventing colic and enterocolitis and improving and/or generally promoting the intestinal well-being of infants and/or young children.

In other words, the present invention relates to a method for improving and/or generally promoting the intestinal well-being of infants and/or young children, comprising the administration of branched maltodextrins to newborn babies and/or to young children. More particularly, the present invention relates to a method for improving the flora of the colon of newborn babies and/or young children, comprising the administration of branched maltodextrins to newborn babies and/or to young children. The present invention also relates to a method for treating or preventing colic and enterocolitis in newborn babies and/or young children, comprising the administration of branched maltodextrins to newborn babies and/or to young children.

In the present invention, the terms or expressions below are given with their definitions such as they appear in European Commission Directive 2006/141/EC of Dec. 22, 2006, published in the Official Journal of the European Union on Dec. 30, 2006, which should consequently be taken into account during the reading and interpretation of the present description, of the examples and of the claims.

Thus, in accordance with Directive 2006/141/EC, Article 2(a), the term "infant" denotes children under the age of 12 months. The term "young children" denotes, according to Article 2(b), children aged between one and three years. The expression "infant formulae" denotes, according to Article 2(c), foodstuffs intended for particular nutritional use by infants during the first months of life and satisfying by themselves the nutritional requirements of such infants until the introduction of appropriate complementary feeding. It should be understood here that the infants may therefore be fed only with infant formulae, or else, in a mixed manner, with said infant formulae used as a supplement to breast-feeding. The expression "follow-on formulae" denotes, according to Article 2(d), foodstuffs intended for particular nutritional use by infants when appropriate complementary feeding is introduced and constituting the principal liquid element in a progressively diversified diet of such infants.

The invention relates to the use of branched maltodextrins for improving the flora of the colon of newborn babies and/or young children. For the purpose of the present invention, the improving of the flora of the colon means a modulation of the intestinal microflora toward more significant "beneficial" bacterial populations to the detriment of bacterial species acknowledged as having a role in the digestive disorders described above.

The present invention also relates to a food composition or formula for feeding infants and/or young children, comprising branched maltodextrins for treating or preventing colic and enterocolitis and improving and/or promoting the intestinal well-being in infants and/or young children.

In the present application, the expression "composition for infant nutrition" is used and relates to both food compositions and formulae intended for feeding infants and those intended for young children, up to the age of approximately three years.

In the present invention, the term "branched maltodextrins (BMDs)" is intended to mean specific maltodextrins identical to those described in patent EP 1 006 128-B1 of which the applicant is the proprietor. This patent describes the obtaining of a branched maltodextrin which differs from standard maltodextrins in particular by virtue of the richness in 1-6 glucosidic linkages. These BMDs have the advantage of representing a source of indigestible fibers beneficial to the metabolism and to the intestinal equilibrium.

According to the present invention, said branched maltodextrins are characterized in that they have:
  between 15% and 50% of 1-6 glucosidic linkages, preferentially between 22% and 45%, more preferentially between 20% and 40%, and even more preferentially between 25% and 35%,
  a reducing sugar content of less than 20%, preferentially between 2% and 20%, more preferentially between 2.5% and 15%, and even more preferentially between 3.5% and 10%,
  a polydispersity index of less than 5, preferentially between 1 and 4, more preferentially between 1.5 and 3, and
  a number-average molecular weight Mn of less than 4500 g/mol, preferably between 400 and 4500 g/mol, more preferentially between 500 and 3000 g/mol, even more preferentially between 700 and 2800 g/mol, and even more preferentially between 1000 and 2600 g/mol.

The present invention thus relates to the use of branched maltodextrins for improving the flora of the colon of newborn babies and/or young children, and thus treating or preventing colic and enterocolitis and improving and/or generally promoting the intestinal well-being of infants and/or young children, characterized in that the branched maltodextrins all have the characteristics set out above.

In particular, use may be made of BMDs having between 15% and 35% of 1-6 glycosidic linkages, a reducing sugar content of less than 20%, a number-average molecular weight Mn of between 250 and 4500 g/mol and a weight-average molecular weight Mw of between 4000 and 6000 g/mol.

According to one variant, said polysaccharide has a molecular weight Mw of between 1000 and 6000 g/mol, preferentially between 1500 and 5000 g/mol, and more preferentially between 3000 and 5000 g/mol.

Certain subfamilies of BMDs described in the abovementioned application may also be used in accordance with the invention. They are, for example, high-molecular-weight BMDs having a reducing sugar content at most equal to 5 and an Mn of between 2000 and 4500 g/mol. Low-molecular-weight BMDs having a reducing sugar content of between 5% and 20% and a molecular weight Mn of less than 2000 g/mol may also be used.

In another advantageous embodiment of the present invention, use may also be made, in accordance with the invention, of the hypoglycemic hyper-branched maltodextrins described in application FR 1 251 810, of which the applicant is the proprietor.

The branched maltodextrins used in accordance with the invention are soluble in water.

For the purposes of the present invention, the term "BMDs" is thus intended to mean maltodextrins of which the 1-6 glucosidic linkage content is greater than that of standard maltodextrins. Thus, standard maltodextrins are defined as purified and concentrated mixtures of glucose and glucose polymers which are essentially 1-4-linked, with only 4% to 5% of 1-6 glucosidic linkages, which have extremely varied molecular weights, which are completely soluble in water and which have a weak reducing power.

The standard maltodextrins are conventionally produced by acid hydrolysis or enzymatic hydrolysis of starch. The classification of standard maltodextrins is based mainly on the measurement of their reducing power, conventionally expressed by the notion of Dextrose Equivalent (D.E.). With regard to this particular point, the definition of maltodextrins reproduced in the Monograph Specifications of the Food Chemical Codex specifies that the D.E. value should not exceed 20. The measurement of the D.E. in fact gives only an approximate idea of the average degree of polymerization (D.P.) of the mixture of constituent glucose and glucose polymers of standard maltodextrins and therefore of their number-average molecular weight (Mn). In order to complete the characterization of the molecular weight distribution of standard maltodextrins, the determination of another parameter is important, that of the weight-average molecular weight (Mw).

In practice, the Mn and Mw values are measured by various techniques. A method of measurement suitable for glucose polymers, which is based on gel permeation chromatography on chromatography columns calibrated with *pullulans* of known molecular weights, is for example used.

The Mw/Mn ratio is called the polydispersity index (P.I.) and makes it possible to characterize overall the distribution of the molecular weights of a polymeric mixture. As a general rule, the molecular weight distribution of standard maltodextrins results in P.I. values of between 5 and 10.

According to one variant of the present invention, the BMDs have a molecular weight Mw of between 1000 and 6000 g/mol, preferably between 1500 and 5000 g/mol, and more preferentially between 3000 and 5000 g/mol.

The BMDs of the present invention are indigestible in nature, the consequence of which is to reduce their calorific value by preventing their assimilation in the small intestine. They therefore provide a source of indigestible fibers beneficial to colonic fermentation and to intestinal equilibrium, which makes them excellent prebiotic candidates for infant nutrition.

By way of indication, their soluble fiber content is generally greater than 80% relative to solids. Their high content of 1-6 glucosidic linkages confers on them entirely particular prebiotic properties: it has in fact emerged that the bacteria of the cecum and of the colon of humans and animals, such as butyrogenic, lactic or propionic bacteria, metabolize highly branched compounds. Furthermore, these BMDs promote the development of bifidogenic bacteria to the detriment of undesirable bacteria. This results in properties that are entirely beneficial to the health of those consuming said BMDs, and more particularly to the health of infants and/or young children.

Finally, the branched nature of said BMDs considerably and advantageously decreases their tendency to retrograde, which makes it possible to envision their use in applications where an absence of retrogradation is necessary, in particular during prolonged storage in an aqueous solution.

It is in fact to the applicant's credit to have discovered that polysaccharides, and more particularly branched maltodextrins, could surprisingly perform the role of prebiotics while making it possible to do away with the negative effects of the other prebiotics known from the prior art and already used in compositions intended for infant nutrition.

The BMDs of the present invention are indigestible in nature, the consequence of which is to reduce their calorific value by preventing their assimilation in the small intestine. They are therefore a source of indigestible fibers beneficial to colonic fermentation and to intestinal equilibrium, which makes them excellent prebiotic candidates for infant nutrition.

By virtue of the numerous abovementioned properties and of the experimental results presented in the examples hereinafter, the BMDs according to the present invention exhibit an improved effect compared with the other prebiotics known from the prior art and already used in infant compositions.

It is actually known that FOSs are not stable with respect to sterilization. This instability results in gradual hydrolysis, which generates undesirable release of glucose and fructose and undesirable coloration. FOSs remain poorly tolerated by the body, which is expressed by the occurrence of diarrhea. It is known from the prior art that the principal prebiotics used today, i.e. mainly FOSs and GOSs, also have negative effects. Besides their effect on the intestinal flora, these FOSs and GOSs also have a noticeable effect on intestinal behavior. In the small intestine, they remain in solution in the chyme and increase the osmotic pressure, creating a call for water in the intestinal lumen. In the colon, bacterial fermentation is accompanied by the production of gas and of short-chain fatty acids which are known to influence intestinal motivity. While these effects are desired in adults in order to improve intestinal transit and prevent constipation problems created by our excessively low-fiber modern diet, the same is not true in infants, where a high consumption of prebiotics can create pathological symptoms, diarrhea, flatulence, colic, etc.

The prebiotics of the present invention make it possible precisely to improve these negative effects and to totally eliminate them.

An example of BMDs particularly suitable for the present invention is the use of Nutriose®, which is a complete range of soluble fibers, recognized for their beneficial effects, and manufactured and sold by the applicant. The products of the Nutriose® range are partially hydrolyzed wheat or corn starch derivatives which contain up to 85% of fiber. This richness in fiber makes it possible to increase colonic fermentation, to improve calorie control, to prolong energy release and to obtain a lower sugar content. In addition, the Nutriose® range is one of the most well-tolerated fibers on the market. It shows higher digestive tolerance, allowing better incorporation than other fibers, thereby representing real dietary advantages.

The specific BMDs used in the present invention meet the criteria for prebiotics in all respects. They are in fact considered to be selectively fermented ingredients which lead to specific changes in the composition and/or the activity of the gastrointestinal microflora and thus exert benefits on the health of the host. A first positive effect exerted by prebiotics, and more particularly the BMDs of the present invention, is their ability to modulate the intestinal flora of infants and/or young children.

Indeed, it emerges from studies carried out by the applicant that the consumption of these BMDs makes it possible to increase the total number of bifidobacteria in a dose-dependent manner. This effect is demonstrated in particular in example 1 hereinafter, where it clearly emerges from the studies carried out that the supplementation, for 44 days, of a conventional diet with 4% of branched maltodextrins makes it possible to increase by approximately 78% the amount of bifidobacteria present in the feces in piglets.

Other studies carried out by the applicant make it possible to demonstrate that the BMDs have a stimulatory effect on bifidobacteria, and more particularly on lactic acid bacteria of *Lactobacillus paracasei* type. This is demonstrated in example 2 of the present invention.

Example 2 also makes it possible to demonstrate that the BMDs according to the present invention also make it possible to inhibit potentially pathogenic bacteria, responsible for the digestive problems discussed above. Indeed, the BMDs of the invention have an inhibitory effect that is greater than the inhibitory effect of other already known fibers, such as GOSs or FOSs. Thus, the inhibitory effect of the BMDs on the growth of *Clostridium difficile, Clostridium perfringens* and *Escherichia coli* is much greater than the inhibitory effect, on said growth, of the other fibers known from the prior art.

According to the invention, the BMDs have a real effect on the inhibition of the bacteria responsible for colic and enterocolitis.

The present invention also relates to the use of BMDs in a composition for infant nutrition, i.e. in a food composition or formula for feeding infants and/or young children.

In one preferred mode of the invention, the use of said BMDs in a composition for infant nutrition is characterized in that the food composition or formula comprises from 0.1% to 45%, preferably from 1% to 20% and even more preferentially from 1% to 10% by dry weight of branched maltodextrins.

According to the present invention, the BMDs may be used alone in food compositions or formulae for feeding infants and/or young children, but may also be combined with other fibers known from the prior art.

Thus, according to one preferential mode of the invention, the use of BMDs in a composition for infant nutrition is characterized in that said composition comprises from 0.1% to 30% of another fiber chosen from fructooligosaccharides (FOSs), inulin, glucooligosaccharides (GOSs), isomaltooligosaccharides (IMOs), transgalactooligosaccharides (TOSs) and any mixtures thereof.

According to one particularly preferred mode, the use of BMDs in a composition for infant nutrition is characterized in that said composition comprises from 0.1% to 45%, preferably from 1% to 20% and even more preferentially from 1% to 10% by dry weight of branched maltodextrins and from 0.1% to 30% of another fiber chosen from fructooligosaccharides (FOSs), inulin, glucooligosaccharides (GOSs), isomaltooligosaccharides (IMOs), transgalactooligosaccharides (TOSs) and any mixtures thereof.

According to the present invention, the prebiotics, and more particularly the BMDs of the composition or formula for infant nutrition, also play an important role in modulating the pH of the stools of infants and/or young children. Indeed, the degrading of the BMDs by the colonic flora generates the formation of short-chain fatty acids, which acidify the intestinal medium.

Thus, the present invention relates to the field of prebiotics in infant nutrition, and more particularly in the nutrition of children under the age of three. The present invention is consequently intended first of all for infants during the first months of their life, when the colonization of the digestive tract takes place. However, it also relates to young children, themselves also victims of digestive problems, or even in more serious diseases, until the introduction of cow's milk into their diet.

The present invention is therefore aimed at both infants and young children who are healthy, but also those who are suffering from a more or less serious dysfunction of their digestive system.

Thus, the present invention relates to the use of BMDs in a composition for infant nutrition, i.e. in a food composition or formula for feeding infants and/or young children for treating or preventing colic and enterocolitis and improving and/or promoting the intestinal well-being in infants and/or young children.

In the present invention, the expression "use of BMDs in a food composition or formula" is understood to mean use of BMDs in any food intended to be given as it is, i.e. in a ready-to-use form, or in a form requiring prior dilution in a consumable liquid or solid support.

In one preferred mode of the invention, the use of BMDs in a composition or formula is characterized in that said composition is in the ready-to-use form, i.e. in the form of soup, compote, yogurt, cereals, fruit juice, tea, cookies or any other food that can be consumed by a child, said food being given at the time of dietary diversification.

In another preferred mode of the present invention, the use of BMDs in a composition or formula is characterized in that said composition or formula is in the form of a powder which needs to be dissolved in any drinkable liquid that can be consumed by children. It may be, inter alia, a powder intended for reconstitution of an infant milk.

In another preferred mode, the use of BMDs in a composition or formula is characterized in that said food composition or formula is in the form of cereals. Actually, starting from 6/9 months, the energy needs of babies increase. Cereals gradually play a role as nutritional supplement to infant milk, which remains, up to 36 months, an essential pillar of the baby's diet.

The present invention also relates to the use of BMDs for producing initial infant formulae. Said initial formulae are intended for feeding infants right from birth. They must meet all the dietary requirements of infants during the first six months of life. However, the initial infant formulae may also be used in combination with supplementary foods, beyond the seventh month and throughout the first year of life.

The present invention also relates to the use of BMDs for producing formulae for infants starting from the age of six months, called follow-on milks.

In another embodiment, the present invention also relates to the use of BMDs for producing formulae for infants starting from the age of six months, called growing-up milks. These milks are consumed by infants aged from approximately ten months to approximately three years. Indeed, from ten months to three years, children still have specific nutritional needs. At this age, infant milk is more suitable than cow's milk.

The compositions or formulae for infant nutrition according to the present invention and containing said BMDs are preferably for feeding infants.

It is accepted in the present invention that the infant formulae are the only foodstuffs resulting from a transformation which totally meet the nutritional needs of infants during the first months of their life until the introduction of an appropriate complementary diet.

The infant formulae described in the present invention are thus for feeding infants right from birth. They must therefore meet all the dietary requirements of infants for the first six months of life.

These formulae are in most cases produced from cow's milk proteins and contain, as carbohydrate sources, only lactose or lactose combined with other carbohydrates.

In order to be as close as possible to the composition of maternal milk, the use of BMDs in a composition for infant nutrition according to the invention is characterized in that said composition may also contain other elements. For example, essential fatty acids may also be added, such as linoleic acid, alpha-linolenic acid, but also arachidonic acid and docosahexaenoic acid. These fatty acids have in fact been identified as having a role in brain development, the development of sight and psychomotor development.

Fatty acids are lipid compounds which essentially participate in the construction and life of cells. Essential fatty acids are fatty acids that the body is not capable of producing and that it must imperatively find in food or food supplements.

Generally, fatty acids and essential fatty acids play an essential role in the correct functioning of cells, in particular for the composition of their membrane and the supply of energy. They also have a role regarding inflammation, immunity and blood coagulation.

There are three types of fatty acids: saturated, monounsaturated and polyunsaturated fatty acids. The overconsumption of saturated fatty acids is not recommended, and should not in any event exceed 30% of the total FAs consumed, since an overconsumption of fatty acids of this type correlates directly with the blood cholesterol level, and therefore with an increase in the risks of cardiovascular diseases.

According to another even more preferential mode of the present invention, the use of BMDs in a composition for infant nutrition is characterized in that said composition may also contain at least one essential fatty acid.

Essential fatty acids are divided up into two groups: the omega-3 fatty acid group and the omega-6 fatty acid group. These two groups are polyunsaturated fatty acids.

The principal fatty acids of the omega-3 group are alpha-linolenic acid, eicosapentaenoic acid and docosahexaenoic acid. They are usually found in algae, "fatty" fish, (mackerel, salmon, tuna, sardine, herring, halibut, anchovy, etc.), and in certain vegetable oils, for instance linseed oil, rapeseed oil and walnut oil. A very large number of studies have demonstrated the positive effects of an omega-3 rich diet in improving the health in general and in cardiovascular health in particular.

The principal fatty acids of the omega-6 group are linoleic acid, which is usually found in vegetable oils, for instance sunflower, grapeseed, evening primrose, wheatgerm and walnut oil; arachidonic acid found in animal flesh (meats) and docosapentaenoic acid found in certain fish and offal.

According to one preferred mode, the use of BMDs in a composition for infant nutrition is characterized in that said composition contains at least one essential fatty acid chosen from the group consisting of alpha-linolenic acid, linoleic acid, arachidonic acid and docosapentaenoic acid, and any mixture thereof.

The low mineralization of women's milk and its richness in vitamins A, E and C, folates and B12, and also in trace elements other than iron with unequalled bioavailability, reinforce the importance of this nutritional side. All these elements are, in addition, suitable for the digestive, enzymatic and especially renal immaturity of the first months of life.

The objective of the use of BMDs in a composition for infant nutrition is characterized in that said composition, on the one hand, is as close as possible, from a nutritional point of view, to the composition of women's milk and, on the other hand, covers as well as possible the energy, mineral and vitamin needs of the child.

In one preferential mode, the use of BMDs in a composition for infant nutrition is characterized in that said composition for infant nutrition also contains at least one element selected from the group comprising fatty acids, vitamins, trace elements, and mineral salts, and mixtures thereof. These elements are essential for the correct development of the child.

Vitamins are substances which do not provide energy, but which are essential to the correct functioning of the organism. They are involved at low concentration in many vital processes. In order to develop harmoniously, our body must have a regular supply of these substances that it cannot synthesize itself (except vitamin D synthesized in the skin under the action of the sun, and vitamins B2 and K synthesized in humans by means of their intestinal flora, but this endogenous production is not sufficient to meet their needs, making it necessary for them to supplement it in their diet).

They are provided by the diet. There are thirteen of them and they are divided up into two categories:
  liposoluble vitamins which are absorbed at the same time as fats and stored. They are soluble in organic solvents. They are vitamins A, D, E and K;
  hydrosoluble vitamins which are not stored over a prolonged time and which are excreted in the urine when they are provided in excess. They are soluble in water. They are vitamins C, B1 or thiamine, B2 or riboflavin, B3 or niacin, B5 or pantothenic acid, B6, B8 or biotin, B9 or folic acid and B12.

According to another advantageous embodiment of the present invention, the use of BMDs in a composition for infant nutrition is characterized in that said composition for infant nutrition may also be supplemented with trace elements. Trace elements are a class of micronutrients required for life but in very small amounts, of about 1 µg, and that the organism cannot produce.

Deficiencies, just like excesses, are detrimental and toxic to the organism. The effect of a trace element depends on the dose taken in. When the trace element is said to be essential, an absence, like an excessive intake, is lethal.

The essential trace elements meet the following criteria:
  are present at a relatively non-variable concentration in the tissues of an organism;
  cause, by their absence, close structural and physiological abnormalities, in the manner similar in several species;
  prevent or correct these disorders by their presence alone.

From a nutritional point of view, it is possible to distinguish two types of trace elements according to the deficiency risk:
  essential trace elements with a demonstrated deficiency risk: iodine, iron, copper, fluorine, zinc, selenium, chromium, molybdenum,
  essential trace elements with a low deficiency risk or a deficiency risk that has not been proven in humans: manganese, silicon, vanadium, nickel and tin.

According to one even more preferential mode, the use of BMDs in a composition for infant nutrition is characterized in that said composition for infant nutrition contains at least one trace element termed essential, chosen from the group consisting of: iodine, iron, copper, fluorine, zinc, and selenium, and any mixtures thereof.

According to another advantageous embodiment of the present invention, the use of BMDs in a composition for infant nutrition is characterized in that said composition for infant nutrition may also be supplemented with at least one mineral salt.

Mineral salts are constituents of the body, of mineral origin. Like vitamins, they are not a source of energy, but are nevertheless essential to life. They are in ionic form (anions or cations).

In the present application, the mineral salts relate to the constituents present in the organism in large amount (a few grams). They are also called macroelements, unlike the trace elements present in small amount, or even in trace amounts, which have already been mentioned in the present application.

The mineral salts in the present application are chosen from the group consisting of sodium, potassium, calcium, chlorides, magnesium, and phosphorus, taken alone or in combination.

According to one even more preferential mode, the use of BMDs in a composition for infant nutrition is characterized in that said composition contains calcium.

Calcium performs an essential role in the forming of the skeleton and the teeth, and also in blood coagulation, muscle activity, hormonal functions, etc. Calcium intakes from the diet are essential since the organism each day eliminates a part of the calcium that it contains.

One of the major advantages of the present invention is that of being able to provide the organism with, in addition to the benefits at the intestinal level provided by the BMDs, all the calcium required daily and for the correct functioning of the organism.

Thus, the use of BMDs in a composition for infant nutrition, which has been supplemented with an element selected from the group comprising fatty acids, vitamins, trace elements and mineral salts, and mixtures thereof, makes it possible to develop formulae for infants and/or for young children, the essential composition of which meets their nutritional needs.

According to another preferential embodiment of the present invention, the use of BMDs in a composition for infant nutrition is characterized in that said composition for infant nutrition also contains nucleotides. A nucleotide is an organic molecule composed of a nucleobase, a pentose and from 1 to 3 phosphate groups. Certain nucleotides form the basis of DNA and RNA, others are cofactors or coenzymes.

According to one preferential mode, the nucleotide is chosen from cytidine 5'-monophosphate, uridine 5'-monophosphate, adenosine 5'-monophosphate, guanosine 5'-monophosphate, and inosine 5'-monophosphate, and any mixtures thereof.

Finally, in another particularly advantageous embodiment of the present invention, the use of BMDs in a composition for infant nutrition is characterized in that said composition also comprises live microorganisms.

The microorganisms in question are probiotic microorganisms chosen from bacteria or yeasts of the genera *Bifidobacterium, Lactobacillus, Lactococcus, Streptococcus, Pediococcus, Enterococcus, Propionibacterium, Saccharomyces* and *Kluyveromyces*, and any mixtures thereof.

According to another preferential mode, the microorganisms are chosen from the species *Bifidobacterium longum, Lactobacillus casei, Lactobacillus rhamnosus, Lactobacilus helveticus* and *Saccharomyces cerevisiae*.

According to one embodiment, the composition comprises an amount of live microorganisms of at least $10^5$, preferably $10^7$, ideally of at least $5 \times 10^7$ CFU/g.

One of the variants of the present invention also relates to the use of BMDs in a composition for infant nutrition, characterized in that said composition may be colored and/or flavored.

In the present invention, the coloration may be provided by a dye for use in foods, considered to be a food additive according to European Directive No 89/107/EEC of Dec. 21, 1988, on the approximation of the laws of the Member States concerning food additives authorized for use in foodstuffs intended for human consumption.

In the present invention, the name "dye" denotes any substance normally not consumed as a food per se and normally not used as a characteristic ingredient in the diet, possibly having a nutritive value, and the intentional addition of which to foodstuffs, for a technological purpose at the stage of their production, transformation, preparation, treatment, packaging, transportation or warehousing, has the effect, or may reasonably be considered to have the effect, that it itself becomes, or that its derivatives become, directly or indirectly, a constituent of the foodstuffs.

In the present invention, the name "dye" denotes any substance artificially added to a food so as to change the color thereof, and to theoretically make it more appetizing. Its origin may be natural (organic or mineral) or synthetic. Examples of food dyes that may be added to the composition or formula for infant nutrition are, for example, curcumin (yellow), cochineal red A (red), chlorophyllins (green), caramel (brown), carotenoids (orange), etc.

Other examples of dyes that can be used in the present invention are also natural pigments, for instance natural pigments of carrot, of lobster, of fish and also natural pigments of flowers, of leaves and of fruits (apricots, red fruits, etc.).

According to the present invention, the use of BMDs in a composition for infant nutrition is characterized in that said composition may also be flavored through the addition of one or more flavors.

In the present invention, the name "flavor" denotes all the substances not intended to be consumed as they are, which are added to foodstuffs to give them an odor and/or a taste or to modify said odor and/or taste. They are derived from or consist of the following categories: flavoring substances, flavoring preparations, flavors obtained by thermal treatment, smoke flavors, flavor precursors or other flavors or mixtures thereof.

The flavoring substances are defined chemical substances, which includes the flavoring substances obtained by chemical synthesis or isolated by chemical processes, and the natural flavoring substances. The flavoring preparations are flavors other than defined chemical substances, which are obtained by means of appropriate physical, enzymatic or microbiological processes, from materials of vegetable, animal or microbiological origin taken as they are or after transformation thereof for human consumption. The flavor precursors, such as carbohydrates, oligopeptides and amino acids, give foodstuffs a flavor via chemical reactions which take place during the transformation of these foodstuffs.

Another variant of the present invention also relates to a composition for infant nutrition for treating or preventing colic and enterocolitis and improving and/or generally promoting the intestinal well-being, comprising branched maltodextrins, characterized in that the branched maltodextrins have:

- between 15% and 50%, preferentially between 22% and 45%, more preferentially between 20% and 40%, and even more preferentially between 25% and 35%, of 1-6 glucosidic linkages,
- a reducing sugar content of less than 20%, preferentially between 2% and 20%, more preferentially between 2.5% and 15%, and even more preferentially between 3.5% and 10%,
- a polydispersity index of less than 5, preferentially between 1 and 4, more preferentially between 1.5 and 3, and a number-average molecular weight Mn of less than 4500 g/mol, preferentially between 400 and 4500 g/mol, more preferentially between 500 and 3000 g/mol, even more preferentially between 700 and 2800 g/mol, and even more preferentially between 1000 and 2600 g/mol.

In one preferred mode of the invention, said composition for infant nutrition comprises from 0.1% to 45%, preferably from 1% to 20% and even more preferentially from 1% to 10% by dry weight of branched maltodextrins.

In another preferred mode of the invention, said composition for infant nutrition comprises from 0.1% to 45%, preferably from 1% to 30% and even more preferentially from 1% to 20% by weight of branched maltodextrins relative to the total weight of the food composition or formula ready to be consumed.

The present invention is therefore aimed at both infants and young children who are healthy, but also at those who are suffering from a more or less serious dysfunction of their digestive system.

Thus, the present invention relates to a composition for infant nutrition, comprising at least branched maltodextrins for treating or preventing colic and enterocolitis and improving and/or promoting the intestinal well-being in infants and/or young children.

In the present invention, the term "food composition or formula" is understood to mean any food intended to be given as it is, i.e. in a ready-to-use form, or in a form requiring prior dilution in a consumable liquid or solid support.

In one preferred mode of the invention, said composition or formula is in the ready-to-use form, i.e. in the form of soup, compote, yogurt, cereals, fruit juice, tea, cookies or any other food that can be consumed by a child, said food being given at the time of dietary diversification.

In another preferred mode of the present invention, said composition or formula is in the form of a powder which needs to be dissolved in any drinkable liquid that can be consumed by children. It may be, inter alia, a powder intended for reconstitution of an infant milk.

In a final preferred mode of the present invention, said composition or formula also contains an element chosen from the group comprising calcium, phosphorus, vitamin B1, vitamin B2, vitamin B12, vitamin B19, vitamin A and vitamin D, and mixtures thereof, and essential fatty acids.

A subject of the present invention is also a granulated powder comprising branched maltodextrins, characterized in that it has a laser volume mean diameter D4,3, of between 10 µm and 500 µm, preferably between 50 µm and 350 µm and even more preferentially between 70 µm and 250 µm, and a solids content, determined by stoving at 130° C. for two hours, of greater than 80%, preferably greater than 85%, and even more preferentially greater than 90%.

In one preferred mode of the present invention, the granulated powder is suspended in any drinkable liquid intended for human consumption.

Thus, the present invention also relates to a liquid composition obtained by dissolving the granulated powder comprising the branched maltodextrins of the present invention, characterized in that the dissolution rate of the granulated powder in the liquid is between 2% and 30% by dry weight, preferably between 2% and 20%, even more preferentially between 3% and 15%, and in particular between 5% and 10%.

Preferably, the granulated powder is dissolved in a liquid chosen from the group consisting of water, fruit juices, fruit nectars, vegetable juices and vegetable nectars.

Even more preferentially, the granulated powder is dissolved in water, it being possible for said water to be spring water, mineral water, or water which is naturally sparkling or sparkling through the addition of carbon dioxide, or non sparkling.

In one preferential mode of the invention, the granulated powder or the liquid composition obtained by dissolving the granulated power according to the invention is used to replace milk of animal origin, and more particularly cow's milk.

In another preferential mode of the invention, the granulated powder or the liquid composition obtained by dissolving the granulated powder according to the invention is used in preparing bottle-feeding foodstuffs, and more particularly in preparing bottle-feeding milks for infants and young children.

The pH can vary according to the liquid chosen for dissolving the granulated powder. Optionally, it can be corrected by any means known to those skilled in the art, and in particular using acids or bases for use in foods.

In another even more preferential mode, the granulated powder or the liquid composition obtained by dissolving the granulated power according to the invention can be supplemented with other elements, in order to satisfy and comply with all the organolectic and nutritional characteristics targeted.

The invention will be understood even more clearly on reading the examples which follow, which are intended to be illustrated, by making reference only to certain embodiments and to certain advantageous properties according to the invention, and nonlimiting.

EXAMPLES

All the examples below were carried with Nutriose® FB06, sold by the applicant company, which can be obtained from wheat or corn and characterized by a fiber content of 85% by dry weight and which contains at most 0.5% by dry weight of DP1-DP2.

Example 1: Effects of Nutriose® on the Level of Fecal Bifidobacteria in Piglets

The objective of this test is to study the effects of Nutriose® FB06 on the level of fecal bifidobacteria in piglets.

The test is carried out on two groups of eight weaned piglets weighing 6.53±0.44 kg at the beginning of the study.

The experimental treatments are the following:

Batch No. 1: control animals fed using a conventional diet containing 4% of dextrose, as reference product, Batch No. 2: animals fed using a conventional diet containing 4% of Nutriose® FB06.

After 44 days of supplementation with one of the two diets, the feces of the animals of the two groups are collected and frozen at −80° C. A real-time PCR analysis makes it possible to determine the levels of bifidobacteria by quantifying the 16S rRNA.

The following table 1 presents the results obtained.

TABLE 1

| results | | | |
|---|---|---|---|
| | Batch No. 1 | Batch No. 2 | p value |
| *Bifidobacterium* spp. (log 10 16S gene copy/g) +/− standard error | 2.39 +/− 0.51 | 4.27 +/− 0.59 | 0.034 |

Batch No. 2 of piglets fed with a conventional diet containing 4% of branched maltodextrins of Nutriose® FB06 type has an approximately 78% higher level of bifidobacteria than batch No. 1 of piglets fed with a conventional diet free of branched maltodextrins.

The results show that the consumption of Nutriose® FB06 for 44 days makes it possible to significantly increase the population of bifidobacteria in piglets.

Example 2: In Vitro Effects of Various Prebiotics on the Digestive Flora

The objective of this in vitro test, carried out in microplates, is to measure the effect of various products on the stimulation or inhibition of the growth of bacteria that can potentially colonize the colon of newborn babies.

The four products tested at 50 mg/ml are Nutriose® FB06, an FOS (Actilight 950P), a GOS (Purimune High Purity) and also the FOS/GOS (1:9) mixture. The solutions obtained are filtered through a 0.22 micron Millipore filter in order to prevent any contamination. The negative control is water.

The bacterial preparations are calibrated at $10^4$-$10^5$ CFU/ml.

The media used, the culture conditions and the bacteria tested are listed in table 1. The growth of each of the bacteria is monitored over time in the presence or absence of the test product with a microplate reader. The reading is carried out at an optical density of 595 nm every hour.

TABLE 2

| bacterial strains used, culture conditions | | |
|---|---|---|
| Strains CIP: Collection Institut Pasteur | Culture media | Culture conditions |
| *Lactobacillus rhamnosus* ATCC 53.103 | Man Rogosa Sharp (MRS) broth | 37° C., aerobiosis |
| *Lactobacillus paracasei* subsp *paracasei* CIP 103.704 | Man Rogosa Sharp (MRS) broth | 37° C., 5% $CO_2$ |
| *Lactobacillus plantarum* CIP A159 | Man Rogosa Sharp (MRS) broth | 37° C., 5% $CO_2$ |
| *Bacteroides fragilis* CIP 105.892 | CIP anaerobic broth | 37° C., anaerobiosis |
| *Bacteroides ovatus* CIP 103.756 | CIP anaerobic broth | 37° C., anaerobiosis |
| *Bacteroides thetaiotaomicron* CIP 104.207 | CIP anaerobic broth | 37° C., anaerobiosis |
| *Clostridium difficile* CIP 104.282 | CIP anaerobic broth | 37° C., anaerobiosis |
| *Clostridium perfringens* ATCC 13.124 | Reinforced clostridia medium (RCM) broth | 37° C., anaerobiosis |
| *Escherichia coli* CIP 53.126 | TS | 37° C., aerobiosis |
| *Campylobacter jejuni* ATCC 29.428 | Columbia + sheep blood, Columbia + horse serum | 37° C., microaerophilic conditions |
| *Enterococcus faecalis* CIP 103.214 | Brain-heart broth | 37° C., aerobiosis |
| *Enterococcus faecium* CIP 102.379 | Brain-heart broth | 37° C., aerobiosis |
| *Klebsiella oxytoca* ATCC 49.131 | TS | 37° C., aerobiosis |
| *Staphylococcus aureus* CIP 4.83 | TS | 37° C., aerobiosis |

TABLE 3 below summarizes the results obtained.

| | | Nutriose | GOS | FOS | FOS/GOS (1:9) |
|---|---|---|---|---|---|
| A | *Lactobacillus rhamnosus* | −13% | −11% | −8% | −12% |
| | *Lactobacillus paracasei* subsp *paracasei* | 30% | 16% | 20% | 42%* |
| | *Lactobacillus plantarum* | −26% | −27% | −15% | −21% |
| B | *Bacteroides fragilis* | −26% | −23% then +15% | −21% | −23% then +13% |
| | *Bacteroides ovatus* | −21% | −15% then +19% | −11% then +8% then −12% | −15% then +20% |
| | *Bacteroides thetaiotaomicron* | −9% | −14% then +12% then −13% | −15% then +10% then −17% | −16% then +11% then −13% |
| | *Clostridium difficile* | −15% | −13% | −12% | −11% |
| | *Clostridium perfrigens* | −13% | −5% | −12% | −10% |
| | *Escherichia coli* | +50%* | −45%* | −26% | −39% |
| | *Campylobacter jejuni* | −11% | −17% | −15% | −17% |
| | *Enterococcus faecalis* | −14% then +4% | −11% then +19% | −9% then +16% | −12% then +25% |
| | *Enterococcus faecium* | −19% then +24% | −11% then +39% | −9% then +7% | −11% then +38% |
| | *Klebsiella oxytoca* | +52%* | −31% | −8% then +25% then −6% | −28% |
| | *Staphylococcus aureus* | −32% | −17% | −12 % then +14% | −15% then +3% |

*40% ≤ growth inhibition or 40% ≤ growth stimulation
A: potentially beneficial bacteria
B: potentially pathogenic bacteria The results show:
- a stimulation of the growth of *Lactobacillus paracasei* subsp *paracasei* with the four products and in particular for the FOS/GOS mixture,
- an inhibition of the growth of *Lactobacillus plantarum* and *Lactobacillus rhamnosus* with the four products and in identical proportions,
- an inhibition of the growth of *Bacteroides fragilis, Bacteroides ovatus, Bacteroides thetaiotaomicron, Clostridium difficile, Clostridium perfringens, Campylobacter jejuni* and *Enterococcus faecium*, in identical proportions for the four products,
- an inhibition of the growth of *Klebsiella oxytoca* and *Staphylococcus aureus* which is more particularly marked with Nutriose® FB06, an inhibition of the growth of *Escherichia coli* which is more particularly marked with Nutriose® FB06 and GOS.

Example 3

Objective of the Test

The objective of this in vivo test is to study the effects of the branched maltodextrins of the Nutriose® FB06 type in axenic mice, inoculated with an enterotoxinogenic strain of *Clostridium perfringens*, on the induction of the mortality of the animals, the regulation of the colonization of the strain at the intestinal level and the regulation of the translocation of the strain. This type of enterotoxinogenic strain is responsible for necrotizing enterocolitis. Indeed, the occurrence of gram-negative septicemia causes the death of newborn babies since this type of strain becomes established in the colon of children and translocates to the peripheral organs.

Protocol 8 or 9 mice per group (males and females) are used in the experiment (axenic C3H/He mice 6 to 8 weeks old). The animals are housed in an isolator.

The *Clostridium perfringens* strain is isolated from a biopsy of a patient suffering from necrotizing enterocolitis. The inoculum is prepared in a Columbia medium supplemented with cysteine hydrochloride and glucose. The inoculation with this strain is carried out by esophageal gavage on D3 of the test.

The amount administered is $10^6$ CFU/animal.

The test products are administered daily in the drink and are sterilized by filtration (0.2μ) and autoclaving (110° C., 30 minutes).

The four groups are the following:

Osmosed water (negative control).

Lactose at 70 g/l; the lactose activates the genes for sporulation and for synthesis of enterotoxins via galactose.

Nutriose® FB06 at 4 g/l.

Nutriose® FB06 at 35 g/l (equivalent to the amount of glucose of the 70 g/l lactose batch).

The total duration of the test is 14 days.

24 hours after the implantation of *Clostridium perfringens*, two animals per group are sacrificed in order to count the strain in various organs.

48 hours after the implantation of *Clostridium perfringens*, feces are collected in order to perform a *Clostridium perfringens* count.

Ten days after the implantation, all the animals are sacrificed in order to count the strain in various organs.

Results—Mortality of the Mice

The results show that 100% of the mice of the water, Nutriose® FB06 at 4 g/l, and Nutriose® FB06 at 35 g/l groups are alive.

100% of the mice of the 70 g/l lactose positive group died between D+2 and D+3. Nutriose® FB06 does not therefore have a lethal effect, contrary to lactose. It may be considered that there is no induction of toxinogenesis whatever the concentration tested.

Results—Implantation of *Clostridium* Perfringens in the Feces (48 h Post-Implantation)

TABLE 4

| | Count (log CFU/g of feces) 48 h post-implantation n = 4 mice/group |
|---|---|
| Water negative control | 8.51 ± 0.26 |
| Nutriose ® FB 06 to 4 g/l | 8.04 ± 0.64 |

TABLE 4-continued

| | Count (log CFU/g of feces) 48 h post-implantation n = 4 mice/group |
|---|---|
| Nutriose ® FB 06 to 35 g/l | 8.25 ± 0.42 |
| Lactose | Mice dead or dying |

The *Clostridium perfringens* count in the feces is identical between the water, Nutriose® FB06 at 4 g/l and Nutriose® FB06 at 35 g/l groups.

These results lead to the prediction of minimum bacterial translocation since the fecal excretion of the bacterium is high.

Results—*Clostridium* Perfringens Colonization in the Digestive System and *Clostridium* Perfringens Translocation (24 h Post-Implantation)

Two mice per group were sacrificed.

The ileum, the cecum, the colon and the Peyer's patches represent the intestinal part, while the blood, the kidneys, the spleen, the liver, the lungs and the *thymus* are the target organs for bacterial translocation.

TABLE 5

*Clostridium perfringens* count in various organs

| Count (log CFU/g) | Water negative control | Lactose | Nutriose ® FB06 at 4 g/l | Nutriose ® FB06 at 35 g/l |
|---|---|---|---|---|
| Ileum | 7.2 ± 0.5 | 3.4 ± 0.8 | 6.7 ± 0.4 | 7.6 (F) |
| Cecum | 8.4 ± 0.3 | 5.5 ± 0.8 | 7.9 ± 0.3 | 8.0 (F) |
| Colon | 7.8 ± 0.1 | 6.6 ± 0.1 | 8.5 ± 0.6 | 8.2 (F) |
| Peyer's patches | 3.5 ± 0.9 | N.D | 3.2 ± 1.0 | 3.9 (F) |
| Blood | N.D | 2.3 (M) | 2 (M) | N.D |
| Kidney | N.D | 3.0 (F) | N.D | N.D |
| Spleen | N.D | 4.2 (M) | 3.7 (F) | N.D |
| Liver | N.D | 4.4 (M) | 3.5 ± 0.3 | 3.0 (M) |
| Lung | N.D | N.D | 3.0 (F) | N.D |
| Thymus | N.D | N.D | 3.7 (M) | 3.6 (F) |
| Number of mice | 2 | 2 | 2 | 2 |

N.D: not detected,
M: male mouse,
F: female mouse

Compared with the control mice, the mice taking lactose show a weak colonization of the intestine. On the other hand, the lactose promotes bacterial translocation, probably in the lower part, since the Peyer's patches are not contaminated.

The mice consuming Nutriose® FB06 at 4 g/l and 35 g/l show intestinal colonization similar to the controls, in line with the results of table 4. The bacterial translocation appears to be limited at the Nutriose® FB06 at 35 g/l.

Results—*Clostridium* Perfringens Colonization in the Digestive System and *Clostridium* Perfringens Translocation (Ten Days Post-Implantation)

TABLE 6

*Clostridium perfringens* count in various organs

| Count (log CFU/g) | Water negative control | Nutriose ® FB06 at 4 g/l | Nutriose ® FB06 at 35 g/l |
|---|---|---|---|
| Ileum | 6.1 ± 0.6 (6) | 6.6 ± 0.7 (7) | 6.5 ± 0.6 (6) |
| Cecum | 8.7 ± 0.1 (6) | 8.8 ± 0.3 (7) | 8.5 ± 0.3 (6) |
| Colon | 8.6 ± 0.5 (6) | 8.3 ± 0.4 (7) | 8.5 ± 0.4 (6) |
| Peyer's patches | 2.5 ± 0.7 (4) | 2.1 ± 0.5 (6) | 2.2 ± 0.7 (6) |
| Blood | 4 (1M) | N.D | N.D |

TABLE 6-continued

Clostridium perfringens count in various organs

| Count (log CFU/g) | Water negative control | Nutriose ® FB06 at 4 g/l | Nutriose ® FB06 at 35 g/l |
|---|---|---|---|
| Kidney | 2.9 (1F) | 3.1 (1) | N.D |
| Spleen | N.D | 3.2 (1) | N.D |
| Liver | 2.8 ± 0.4 (2) | N.D | N.D |